(12) United States Patent
Hjertman et al.

(10) Patent No.: US 6,689,101 B2
(45) Date of Patent: Feb. 10, 2004

(54) MEDICAL ARRANGEMENT

(75) Inventors: Birger Hjertman, Vällingby (SE); Jonas Fridholm, Bromma (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/862,677

(22) Filed: May 22, 2001

(65) Prior Publication Data

US 2002/0007142 A1 Jan. 17, 2002

Related U.S. Application Data

(60) Provisional application No. 60/211,119, filed on Jun. 12, 2000.

(30) Foreign Application Priority Data

May 22, 2000 (SE) .............................................. 0001893

(51) Int. Cl.[7] .............................................. A61M 37/00
(52) U.S. Cl. ...................... 604/131; 604/131; 604/218; 604/217; 604/191; 604/68; 604/70
(58) Field of Search ................................. 604/187, 218, 604/217, 70, 131, 68, 191

(56) References Cited

U.S. PATENT DOCUMENTS

| | | | |
|---|---|---|---|
| 2,591,046 A | | 4/1952 | Brown |
| 2,821,981 A | | 2/1958 | Ziherl et al. |
| 3,138,257 A | | 6/1964 | Andersen |
| 3,908,651 A | * | 9/1975 | Fudge ........................ 128/173 |
| 4,447,225 A | | 5/1984 | Taff et al. |
| 4,581,015 A | * | 4/1986 | Alfano ........................ 604/88 |
| 4,623,332 A | * | 11/1986 | Lindmayer et al. ............ 604/68 |
| 4,650,475 A | * | 3/1987 | Smith et al. ................. 604/411 |
| 5,472,422 A | | 12/1995 | Ljungquist |
| 5,501,673 A | | 3/1996 | Hjertman et al. |
| 5,520,639 A | * | 5/1996 | Peterson et al. .............. 604/68 |
| 5,620,434 A | * | 4/1997 | Brony ........................ 604/406 |
| 5,716,338 A | | 2/1998 | Hjertman et al. |
| 5,743,890 A | | 4/1998 | Hjertman et al. |
| 5,817,055 A | | 10/1998 | Ljungquist |
| 5,833,661 A | | 11/1998 | Trapp et al. |
| 5,879,336 A | * | 3/1999 | Brinon ........................ 604/191 |
| 5,879,340 A | * | 3/1999 | Epstein ........................ 604/313 |
| 5,989,221 A | * | 11/1999 | Hjertman ..................... 604/131 |
| 6,117,212 A | * | 9/2000 | Buechele et al. ............. 95/266 |
| 6,146,362 A | * | 11/2000 | Turnbull et al. ............. 604/256 |
| 6,203,521 B1 | * | 3/2001 | Menne et al. ................. 604/68 |
| 6,440,105 B1 | * | 8/2002 | Menne ........................ 604/218 |
| 2002/0007143 A1 | * | 1/2002 | Gordon ........................ 604/70 |

FOREIGN PATENT DOCUMENTS

DE 19900827 1/1999

* cited by examiner

Primary Examiner—Ira S. Lazarus
Assistant Examiner—Tu Cam Nguyen
(74) Attorney, Agent, or Firm—Dinsmore & Shohl LLP

(57) ABSTRACT

An injector device for delivery of liquid from a high pressure, the device comprising a housing, a pressure chamber 2 comprising a pressure barrel 4 for accommodation of at least one piston therein and having a front end opening 6 for ejection of the liquid, the pressure chamber being of sufficient strength to sustain the liquid pressure. The device further comprises a storage chamber 16, separate from the pressure chamber, for the liquid or the liquid precursor components, and a conduit 22 between the pressure chamber and the storage chamber. A pressurizing mechanism 26 in the housing is arranged to apply force, directly or indirectly, on the piston in the pressure barrel to create said liquid pressure. The pressure chamber, the piston and at least a part of the conduit is arranged as a unit, wherein said unit and the housing have corresponding fitting parts allowing releasable attachment of the unit to the housing in a position permitting fluid connection between storage chamber and pressure chamber through the conduit and permitting the pressurizing mechanism to act on the piston.

65 Claims, 10 Drawing Sheets

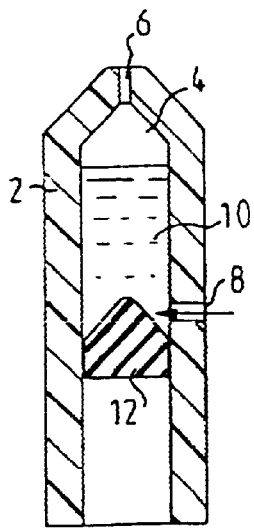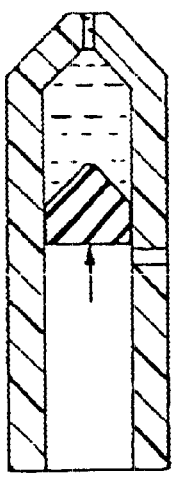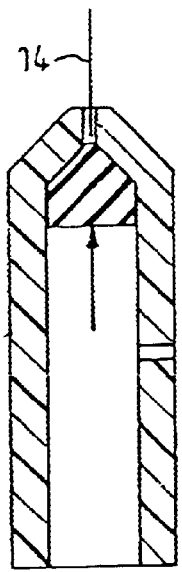
FIG.1A     FIG.1B     FIG.1C
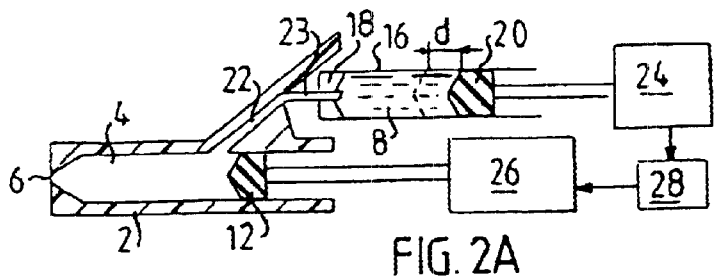
FIG.2A
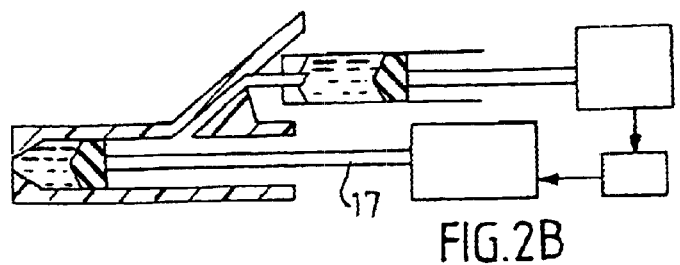
FIG.2B

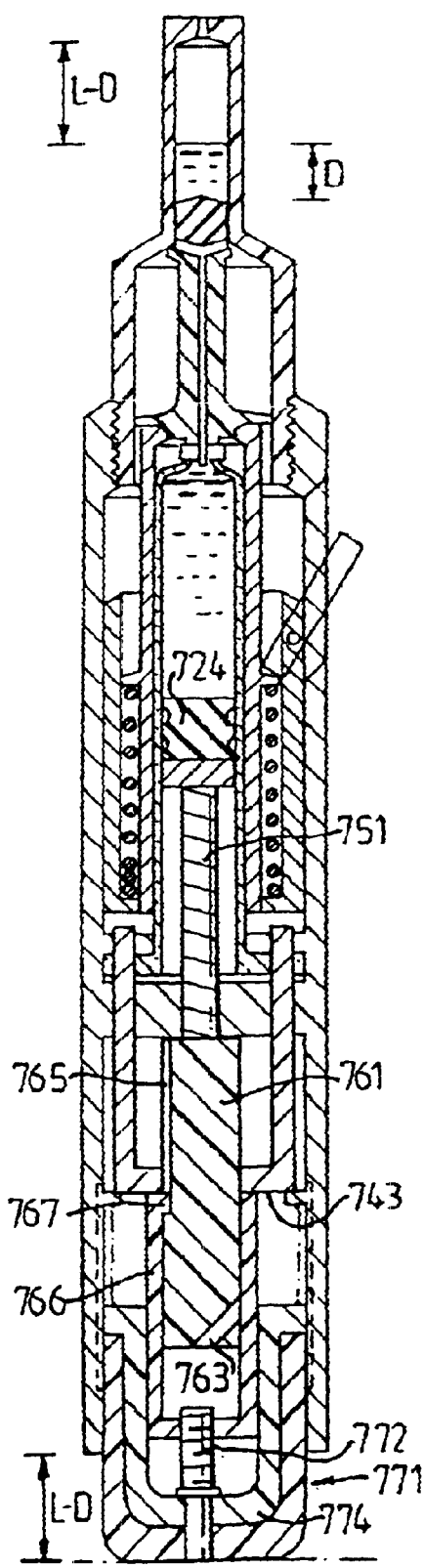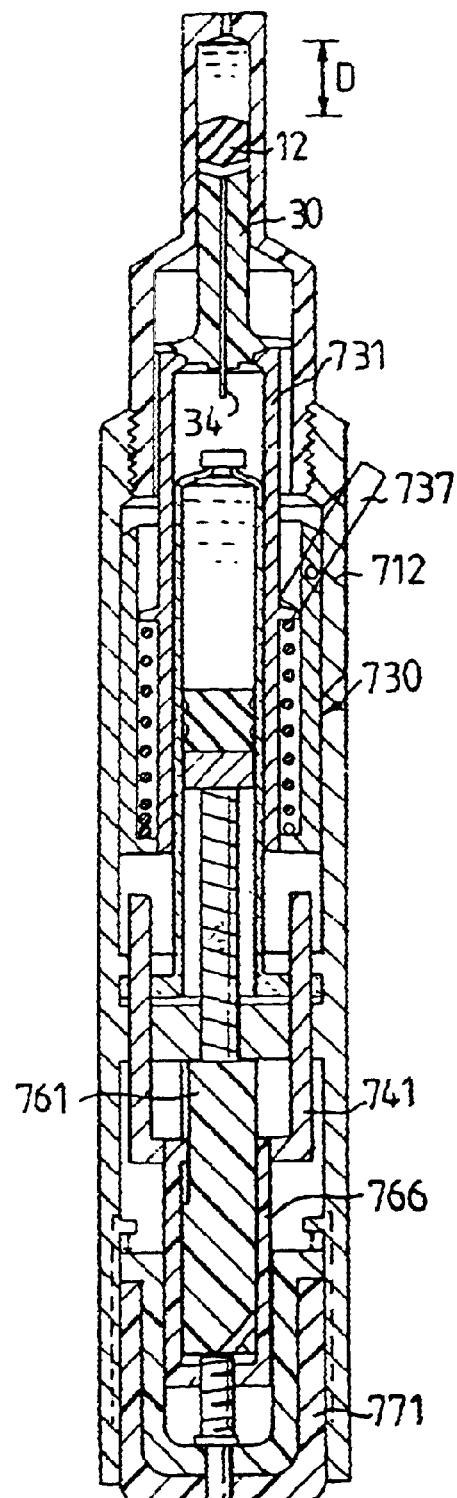
FIG.7B
FIG.7C

MEDICAL ARRANGEMENT

RELATED APPLICATION

The present application claims priority under 35 U.S.C. § 119 of U.S. application Ser. No. 60/211,119 filed Jun. 12, 2000.

FIELD OF THE INVENTION

The present invention relates to an injector device, an injector unit with a pressure chamber and a method to perform the injection, according to the preambles of the independent claims.

BACKGROUND OF THE INVENTION

The principles of the present invention can be used in connection with any injector requiring high level pressurization of the fluid to be injected. High pressures may be needed for expelling high viscosity product, such as products in oil, gelled, paste, amorphous or suspension form, e.g. for dental purposes or to form slow release deposits in the body. Another major injector type requiring high pressure is jet injectors for needle-less skin penetration of a pressurized liquid to be further discussed below. Although for convenience the invention will be described in terms of such jet injection, the invention shall not be regarded as restricted thereto but shall be understood to embrace other high pressure applications as well.

Jet injection apparatuses for hypodermic jet injection of medical liquids through the skin surface or the mucous membrane of either humans or animals under sufficiently high pressure to force the liquids to a predetermined depth within the tissue beneath the skin surface or mucous membrane are known in the art since many years.

A multi-shot injector instrument employing the jet injection principle is known from U.S. Pat. No. 2,821,981. In this known instrument the fluid to be injected is charged into a distal pressure chamber, an ampoule, from a proximal fluid medicine chamber, e.g. in the form of a conventional syringe. One mechanism is used to transfer the fluid from the fluid chamber into the pressure chamber and another mechanism is then used to perform the injection. Non return valves are provided in the transfer bore to ensure that no back flow occurs. The mechanically rather complicated structure of the injector instrument makes it rather expensive to manufacture. Another drawback with this type of complicated mechanical instruments is the difficulty to assemble the device in a sterile environment. It is sometimes today a demand to make parts non-reusable (disposable) that might be contaminated during injection. This demand is very difficult to fulfill for a device of the type disclosed in U.S. Pat. No. 2,821,981, or generally for mechanically complicated devices of this kind, due to the large number of different parts making up the device.

U.S. Pat. No. 3,138,257 discloses an injector device similar to the one of U.S. Pat. No. 2,821,981.

U.S. Pat. No. 4,447,225 discloses a multi-dose jet injector adapted to receive a medicament bottle or vial from which the medicament liquid is transferred into a transfer chamber. The medicament is then pumped through a one-way valve via a cannula to a medicament delivery chamber. The medicament is then ready for jet injection delivery, which is performed by imparting an ejecting force on the medicament liquid and thus expelling it through an orifice of the jet injector. One drawback with the jet injector disclosed in U.S. Pat. No. 4,447,225 is that it is structurally complicated, e.g. the two step transfer of the medicament liquid prior injection, and thus expensive to manufacture.

U.S. Pat. No. 2,591,046 discloses a hypodermic syringe assembly with two chambers separated by a by-pass section. The liquid medicine is transferred into a distal chamber via the by-pass section. There are no separate chambers able to provide different properties, e.g. resistance against high pressures.

Liquid medicaments intended for injection are ordinarily stored in glass containers prior loaded into a syringe for injection. A rubber seal then seals the glass container. Thus, the liquid medicament is only in direct contact with glass and rubber. The major reason for not using plastic materials as material for medical storage containers is that the plastic material does not provide an entirely closed sealing with regard to oxygen moving into or components out from the container. Also components from the manufacture might be deposed in the plastic material that can affect liquid stored in the container. Another reason is that plastic material may give off trace amounts of components that are unacceptable in injectable preparations. The above mentioned drawbacks regarding plastic material used for medical storage containers are valid only when using plastic containers for normal medical storage times, e.g. up to 2 years. When using plastic materials in e.g. syringes etc. where the liquid medicine only contacts the plastic material when the injection is to be performed the above mention drawbacks can not be identified.

In jet injectors using glass containers, the glass container must resist the high pressure used to expel the liquid from the container. The glass container is then preferably manufactured from hardened glass, which renders it expensive. On the contrary, plastic materials can easily provide the necessary properties for a pressure chamber, such as strength and resilience with low shattering risks. Glass materials for storage chambers and plastic materials for pressure chambers are also suitable for disposable single-use components.

The object of the present invention is to achieve an easy to use injector device that is less expensive to manufacture than those known from the prior art. Another object of the present invention is to achieve a device not having the above-mentioned drawbacks regarding the sterile handling of parts of the device. A further object is to offer an injector device suitable to be pre-filled with medical and allowing storage over extended periods of time before injection and wherein all surfaces of the device and its parts being or coming into contact with the medical can be kept sterile during manufacture, storage and use. Yet another object is to offer a device suitable for ejection of multiple doses from a storage chamber. Still an object is to offer a device suitable for easy exchange and disposal of parts possibly being contaminated during an injection. Still another object of the present invention is to achieve a device provided with sterile parts that inherently cannot be reused in order to prevent unauthorized sterilization and reselling of already used devices that might be dangerous to patients. The invention also has for object of providing corresponding methods for delivery of liquid from high pressure sources.

SUMMARY OF THE INVENTION

The above-mentioned object is achieved by an injector device, a unit with a pressure chamber and a method of performing the injection, according to the characterizing portions of the independent claims.

Preferred embodiments are set forth in the dependent claims.

An easy to use injector device is thus achieved having few movable parts and being easy to manufacture. The injector can be used for any high pressure injector application, can be pre-filled with medical and stored without deterioration of the medical and can be manufactured, stored and used under sterile conditions.

The injector device according to the invention is preferably intended for multi dose injections.

It comprises a separate unit that includes a pressure chamber that is not reusable. The used unit is disposed after use and a new unit is attached to the injector housing when a new injection is to be given.

According to one preferred embodiment of the invention the liquid is pressed into the pressure chamber from the storage chamber, resulting in that no suction of the liquid into the pressure chamber has to be performed which is structurally more complicated to achieve.

According to another preferred embodiment the mechanism is responsible for dosing of the liquid medicine separate from the injection mechanism.

Information from the dosing unit regarding the dose volume transferred from the storage chamber via the liquid conduit into the pressure chamber is supplied to a control arrangement that in turn generates a control signal to a pressurizing mechanism, either as an electrical signal or as a mechanical movement. The control signal controls the movement of a piston in the pressure chamber so that it moves to a position where no air is left in the pressure chamber.

According to still another embodiment of the invention is a mechanical dosing unit used, e.g. by a rotating movement. This movement is stored in a mechanical (or electronic memory) in order to be used by the pressurizing mechanism.

SHORT DESCRIPTION OF THE APPENDED DRAWINGS

FIGS. 1A–1C schematically illustrate different steps of the method according to the invention.

FIGS. 2A and 2B illustrate the injector device according to a first embodiment of the invention and FIGS. 2C and 2D illustrate a control arrangement in a similar device.

FIGS. 7A to 7F illustrate a mechanism for dose setting, de-aeration and injection, usable with the arrangement embodiment of FIG. 3.

Figure 7A:
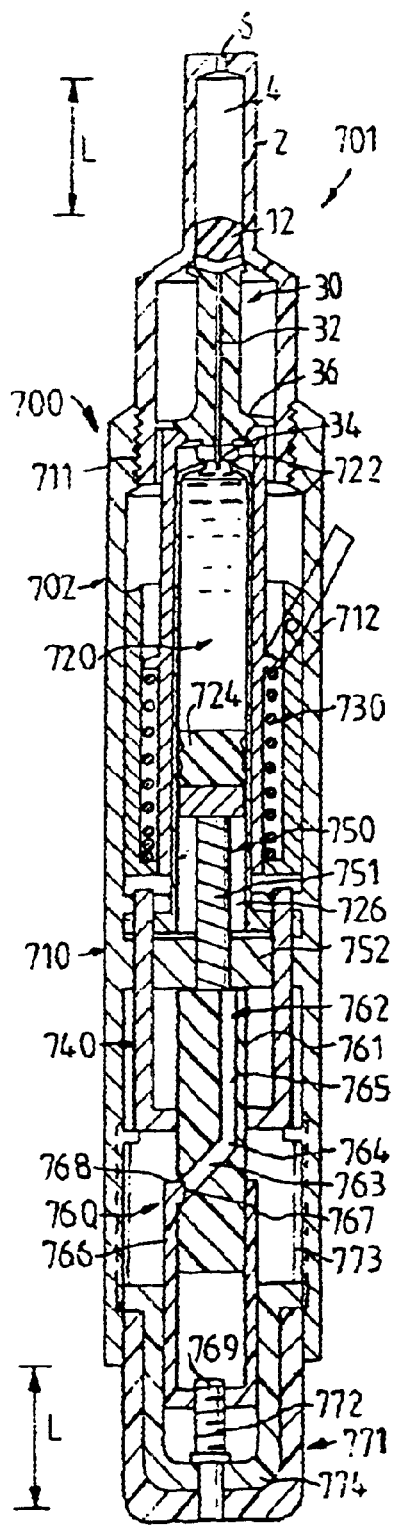
Figure 7D:
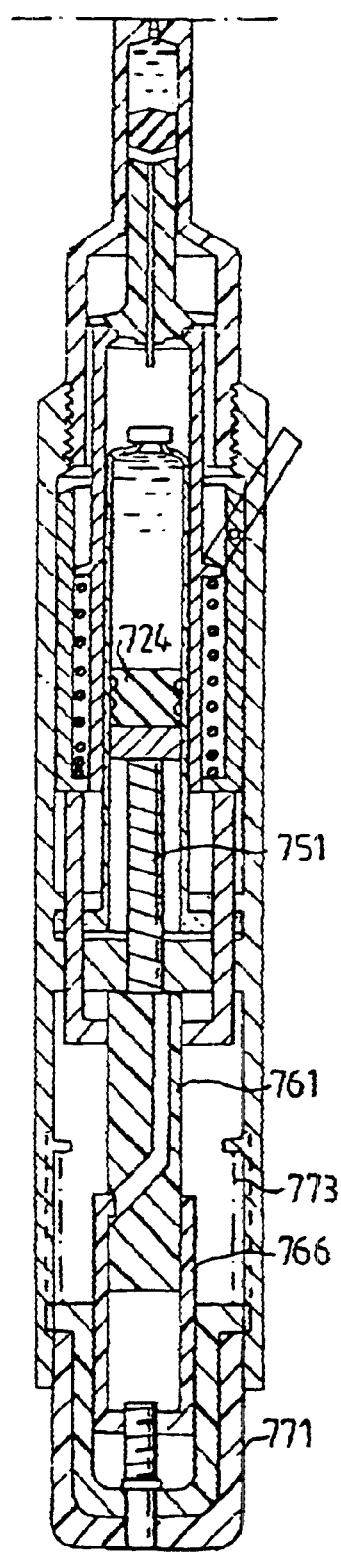
Figure 7E:
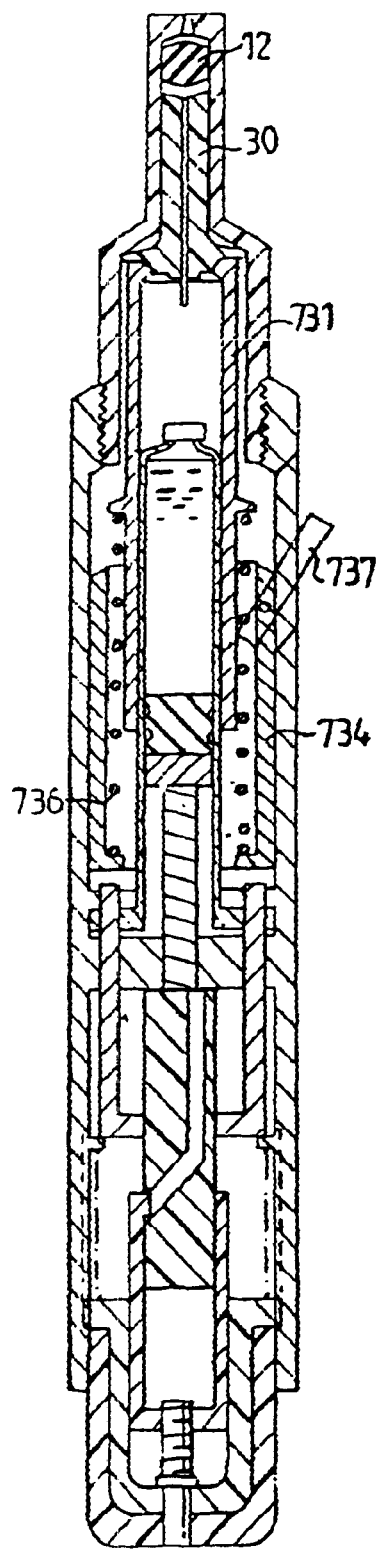
Figure 7F:
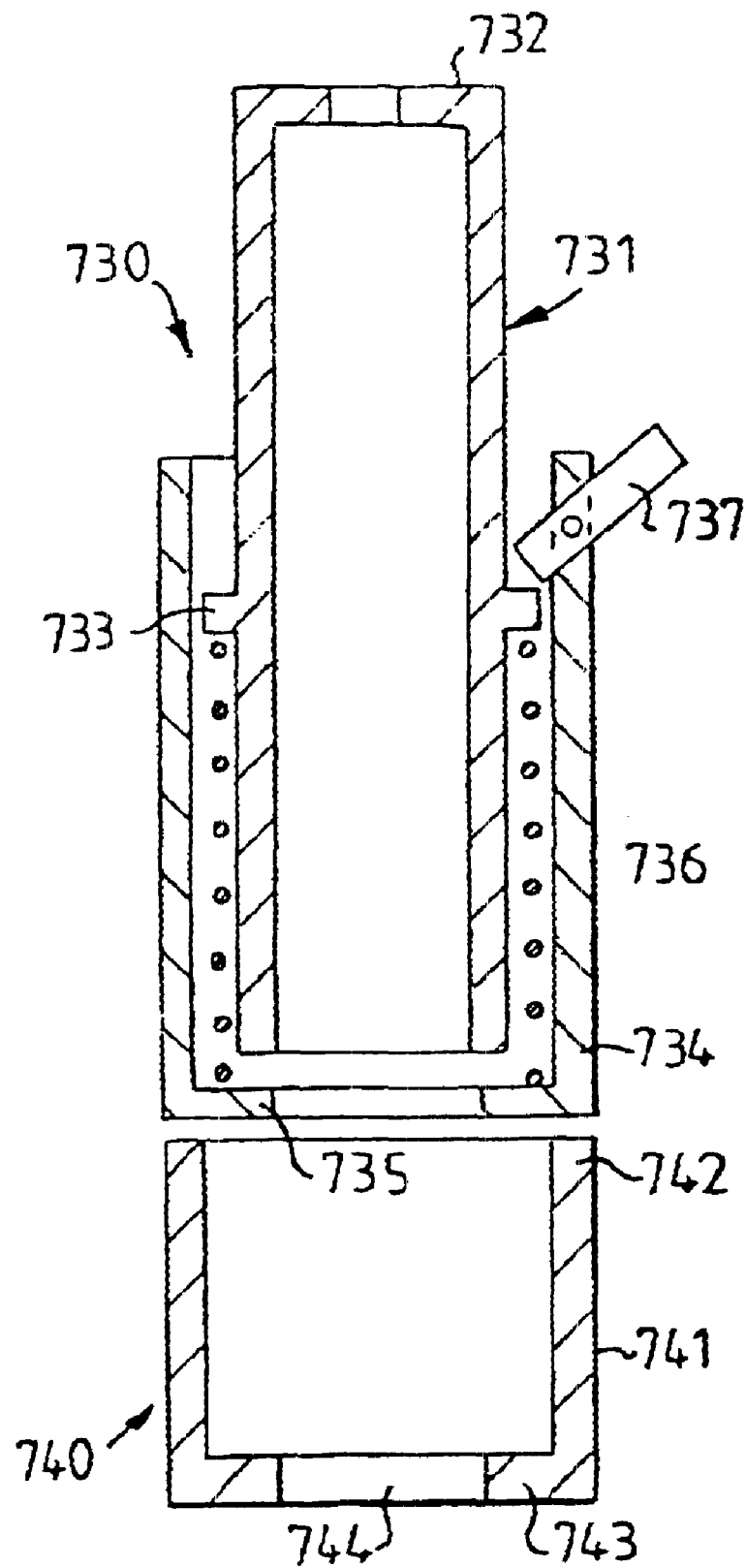
Figure 10:
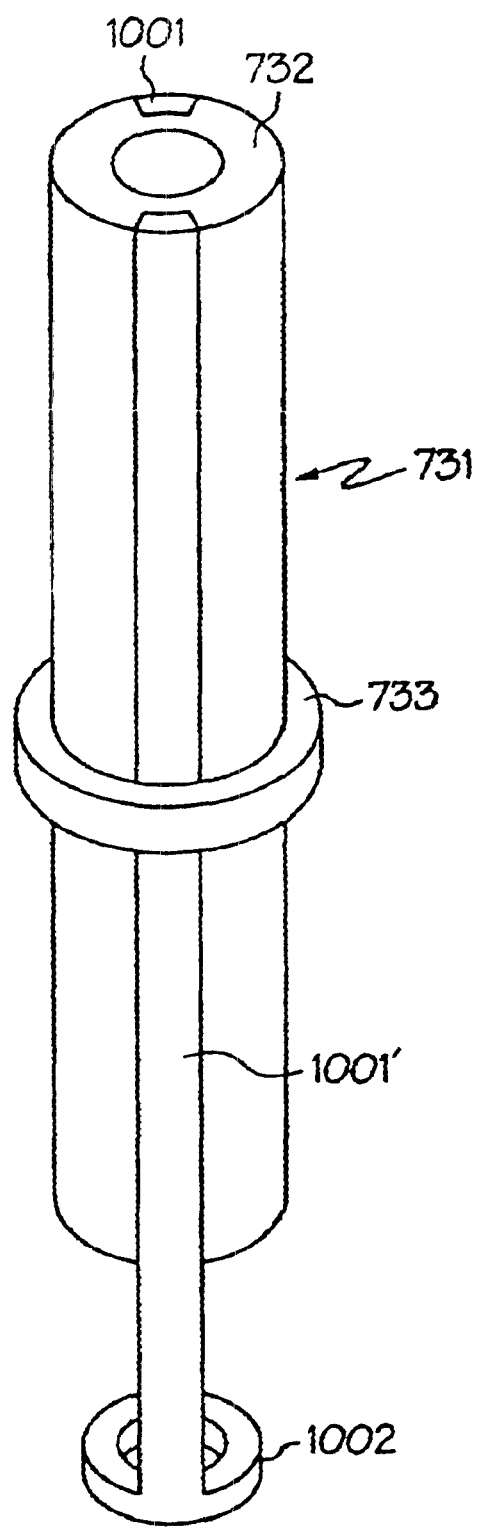

FIG. 10 schematically shows a perspective view of a modification of the ram sleeve of FIG. 7F.

DETAILED DESCRIPTION OF PREFERRED EMBODIMENTS OF THE INVENTION

Corresponding features have the same reference numbers in all figures.

The basic steps in the method according to the present invention are schematically illustrated in FIGS. 1A–1C.

A pressure chamber 2 comprising a pressure barrel 4 provided with a front end opening 6 for ejection of the liquid, an opening 8 for receiving liquid medicine 10 from a storage chamber (not shown) and a piston 12 sealingly inserted in the pressure barrel.

FIG. 1A illustrates the loading step when a predetermined volume of liquid is inserted into the pressure barrel via the opening 8. The volume inserted is less than the volume of the pressure barrel above the piston 12. In this step the piston is in its loading position. The up-right position of pressure chamber in combination with surface tension prevents the transferred liquid to escape through the opening 6. As can be seen from the figure the opening is close to the piston in order to be able to fill the pressure barrel from the bottom forcing the air in a direction towards the opening.

FIG. 1B illustrates the sealing step where the piston 12 has been moved from the loading position to a sealing position and thereby seals off the opening 8 from the storage chamber. The distance that the piston has moved is related to the volume of the liquid medicine such that substantially all air is expelled from the pressure chamber via the front end opening when the piston is in its sealing position. The figure shows a situation where a maximum dose of liquid is transferred into the pressure chamber. If the dose is smaller the piston is of course in a more distal position.

FIG. 1C illustrates the ejecting step where a force is applied on the piston forcing it in a distal direction and thereby ejecting the liquid medicine through the front end opening as a liquid jet 14.

FIGS. 2A and 2B illustrate the injector device according to a first embodiment of the invention.

An injector device for delivery of liquid from a high pressure source is shown including a pressure chamber 2 comprising a pressure barrel 4 for accommodation of at least one pressure piston 12 inserted in the pressure barrel and having a front end opening 6 for ejection of the liquid 8. The pressure chamber being of sufficient strength to sustain the liquid pressure during the injection, and is preferably disposable and made from plastic.

The device further comprises a storage chamber 16, separate from the pressure chamber, for the liquid or the liquid precursor components. The storage chamber is preferably made from glass and has a cylindrical shape. The chamber is provided with a membrane 18 at one end and a movable sealing storage piston 20 inserted from the other end. The membrane and the piston enclose the liquid.

A conduit 22 is arranged between the pressure chamber and the storage chamber. The conduit is preferably an integral part of the pressure chamber and is provided with a needle 23 having a channel in connection with the conduit. The needle is adapted to penetrate the membrane 18 of the storage chamber in order to establish a fluid connection between the storage barrel 8 and the pressure barrel 4.

The device also comprises a dosing unit 24, a pressurizing mechanism 26 and a control unit 28.

The dosing unit is adapted to apply a force on the storage piston inside the storage chamber in order to transfer a predetermined volume of liquid from the storage chamber via the conduit into the pressure barrel. The volume that is transferred is dependent on the distance d moved by the storage piston. The dashed line indicates the position of the storage piston when a dose has been transferred.

The pressurizing mechanism is arranged to apply a force on the pressure piston in the pressure barrel to create the liquid pressure.

The pressurizing mechanism arranged to apply force, directly or indirectly, on the piston. The mechanism is only schematically indicated in the figures and may be e.g. spring loaded as disclosed in U.S. Pat. No. 4,447,225. According to another principle is the injecting force generated by gas under pressure. These two principles are well known in the art. The pressure inside the pressure chamber during injection is in the order of 4000 psi (Pounds per square inch).

When a dose has been transferred into the pressure barrel information regarding the transferred volume is applied from the liquid transfer unit to the control unit 28. The control unit controls the pressurizing mechanism to first move the pressure piston in the pressure barrel from the loading position (FIG. 2A) to the sealing position (FIG. 2B). This movement is related to the volume so that when the pressure piston 12 is in the sealing position substantially all air is expelled from the pressure barrel through the front end opening. After that the pressurizing mechanism generates, on demand, the necessary force to expel the liquid through the front end opening. This is here illustrated as a forward movement of a plunger 17 with respect to the pressurizing mechanism 26.

Figure 2C:
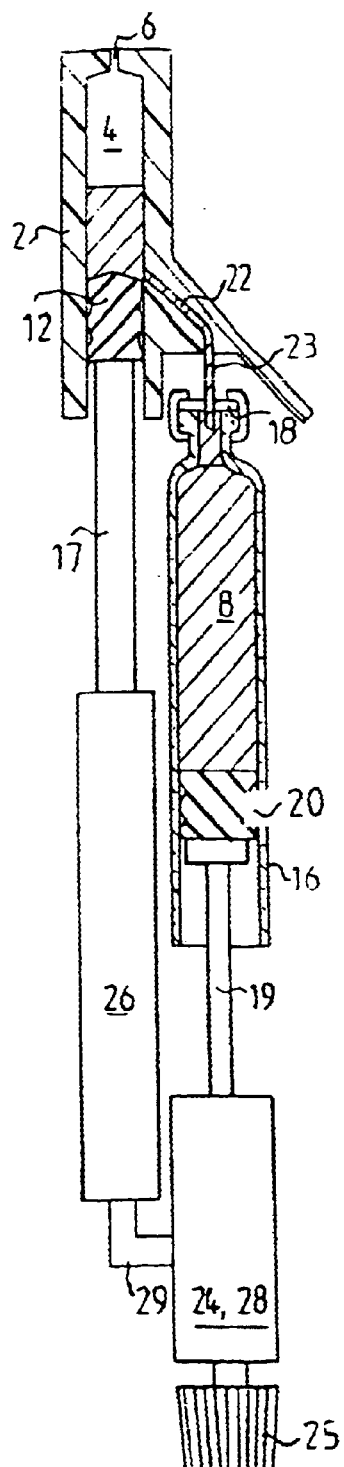
Figure 2D:
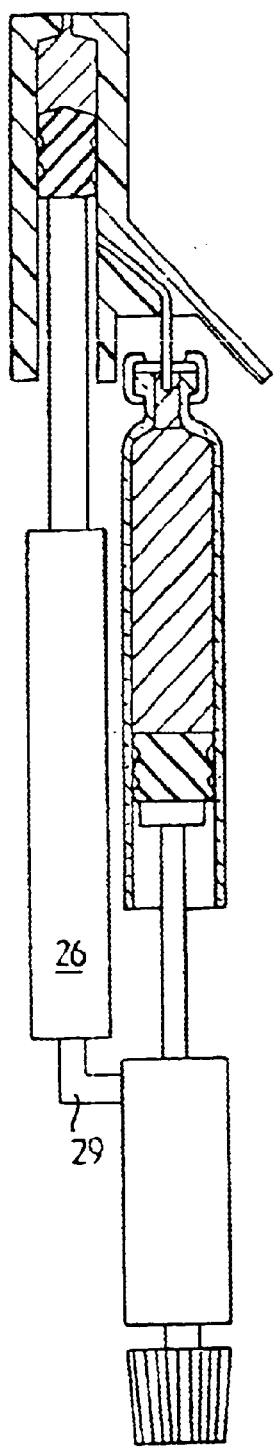

FIGS. 2C and 2D illustrate a similar design with a slightly different layout of the rear control parts. The dosing unit 24 is equipped with a dose setting button 25 and any known arrangement can be used to transform a rotation and/or an axial displacement of the button 25 into a forward movement of a pusher 19 for storage piston 20, e.g. a screw and nut arrangement, for dosing of liquid through conduit 22 and into the pressure chamber 2. FIG. 2C shows the device after that such a dose transfer has taken place but before de-aeration. FIG. 2D shows the device after de-aeration. Between the Figures the pressurizing mechanism 26 has moved forwards with respect to the pressure chamber 2 and also with respect to the box containing the dosing unit 24 and the control unit 28, as evident from the different location of a connection 29 therebetween, but plunger 17 has not moved forward with respect to the pressurizing mechanism 26. The control mechanism is arranged to give a larger forward displacement of the pressurizing mechanism at smaller dose transfer movements for button 25 and vice versa so that the de-aeration forward movement of pressurizing mechanism 26 is complementary to the dose volume transferred to the pressure chamber 2. After de-aeration the pressurizing mechanism can be triggered to perform the injection. The axial mobility of the pressurizing mechanism with stationary plunger facilitates design of this part, e.g. with a spring and trigger, as it need not contain any arrangements for de-aeration.

The pressure chamber, the piston inside the pressure barrel and at least a part of the conduit is arranged as a separate unit that preferably is disposable. The storage chamber 16, the pressurizing mechanism, the dosing unit and the control arrangement are arranged in a housing.

The separate unit and the housing have corresponding fitting parts allowing releasable attachment of the unit to the housing in a position permitting fluid connection between the storage chamber and the pressure chamber through the conduit and permitting the pressurizing mechanism to act on the piston.

FIGS. 3A–3E illustrates the injector device according to a second embodiment of the invention.

The FIGS. 3A–3E shows a cross sectional view of the pressure chamber 2 comprising a pressure barrel 4 provided with a front end opening 6 and a piston 12 arranged inside the barrel. The pressure chamber further comprises a piston rod 30 with a central channel 32 connected to a needle 34, and a rear support 36. A by pass section 38 is further provided at the inner surface of the pressure barrel where the piston is located in its loading position. A part of the storage chamber 16 with the membrane 18 is also shown in the figure. A ram 40 (partly shown in the figure) is in mechanical connection with the pressurizing mechanism (not shown) and adapted to submit the force generated by the pressurizing mechanism to the piston via the support 36 and the piston rod 30. The ram is freely moveable in relation to the storage chamber.

The support 36 preferably comprises a number of support arms, e.g. 3–5, at a proximal part of piston rod. The support positions the needle in a central position of the pressure chamber and ensures that the needle is in a steady position when the needle penetrates the membrane of the storage chamber. The support is also a support for the ram 40 when moving the piston rod and the piston in a distal direction.

The by-pass section 38 may be arranged in many different ways. According to one preferred embodiment a number of traces or channels for the liquid are provided in the inner surface of the pressure barrel. According to another embodiment is the inner surface provided with means that causes deformation of the piston when passing, thereby ensuring that liquid can pass the piston. Persons skilled in the art are aware of many other alternative ways of arranging the by-pass section.

Figure 4A:
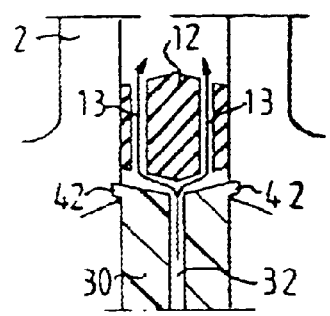
FIGS. 4A and 4B show a cross sectional view of an alternative embodiment of the by-pass section according to the invention.
Figure 4B:
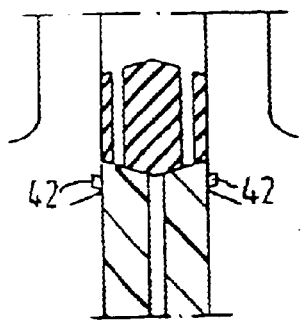

FIGS. 4A and 4B shows a cross sectional view of an alternative embodiment of the by-pass section. According to this embodiment the piston 12 is provided with a number of channels 13, e.g. 1–4. In the loading step of the procedure the channels provide a fluid connection between the central channel 32 of the piston rod 30. In the sealing step the piston rod 30 is in fluid tight connection with the piston and thereby seals off the channels (FIG. 4B).

Figure 3E:
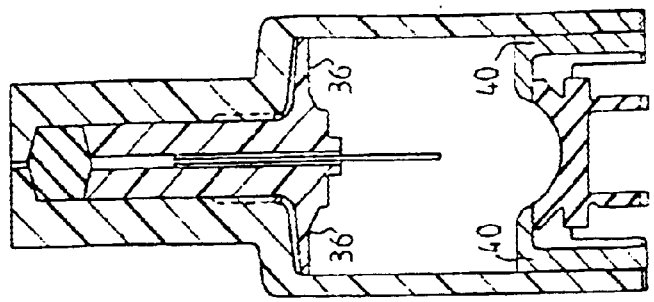
FIGS. 3A–3E illustrate the injector device according to a second embodiment of the invention.
Figure 3D:
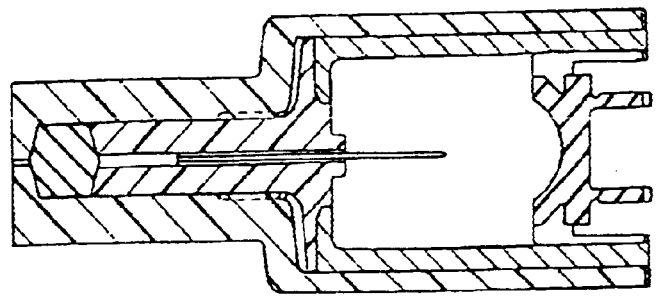
Figure 3C:
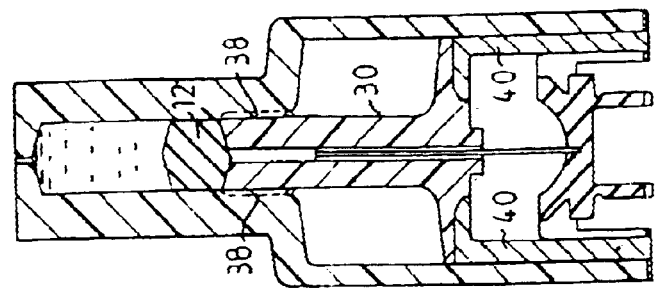
Figure 3B:
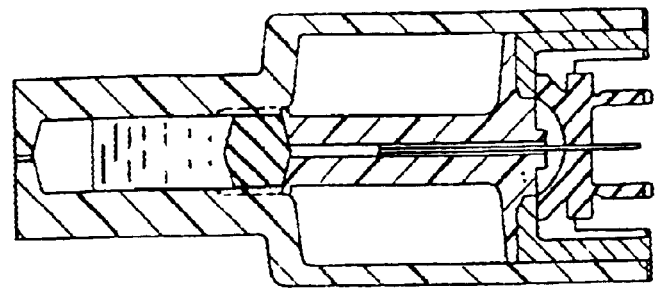
Figure 3A:
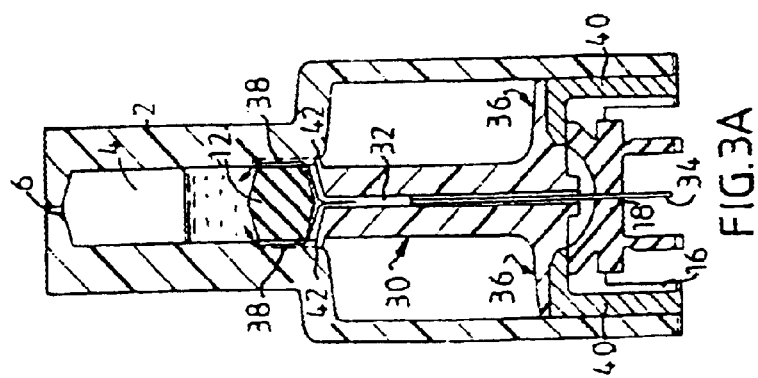

FIG. 3A shows the loading step of the method. A predetermined dose of liquid medicine is expelled from the storage chamber by the dosing unit (not shown). The separate unit comprising the pressure chamber, the liquid conduit, the piston and the piston rod is arranged in connection with the housing (not shown). The upper part of the piston rod is provided with a sealing member 42 that in the loading position engages the inner surface of the pressure barrel in order to achieve a fluid tight connection for the liquid conduit. The needle is inserted through the membrane 18 into the storage chamber. The dose is transferred from the storage chamber through the needle and the central channel of the piston rod and passes the piston in the space between the distal part of the piston rod and the by pass section 38 into the pressure barrel 4.

When the predetermined volume has been transferred into the pressure barrel control arrangement (not shown) receives information from the dosing unit related to the transferred volume and initiate the second step, the sealing step, where the piston is moved from the loading position to the sealing position.

FIG. 3B illustrates the beginning of that step. The ram 40 forces the piston rod in a distal direction. The sealing is torn off from the piston rod and remains in engagement with the inner surface of the pressure chamber as a fluid-tight sealing.

The piston rod has come into contact with the piston, which closes the liquid conduit and enables piston pushing.

In FIG. 3C the piston 12 has been moved a predetermined distance to the sealing position by the ram that exerts a force at the piston via the piston rod 30. The predetermined distance that the piston has been moved is related to the volume of the dose transferred into the pressure barrel such that substantially all air is expelled through the front end opening 6 and that the piston has been moved passed the by pass section 38. During forward movement of the piston rod 30 the needle 34 is withdrawn from the storage chamber, which is arranged stationary with respect to the pressure chamber 2. The injector device is know ready to perform the injection.

FIG. 3D illustrates the end of the ejecting step. A force has been applied to the piston by the ram 40 via the piston rod 30 forcing the piston in a distal direction and thereby ejecting the liquid medicine through the front end opening as a liquid jet. During this final forward movement of the piston rod the needle 34 is fully withdrawn from the storage chamber 2 and out from its sealing membrane 18.

In FIG. 3E the ram 40 is withdrawn from the support of the piston rod and the separate unit (consisting of the pressure chamber, the pressure barrel, the piston and the piston rod with needle) may be released (e.g. unscrewed) from the housing and disposed. The needle is well protected by the pressure chamber when the separate unit is to be released.

One important detail is that the piston is freely movable in relation with the piston rod. This means that the piston rod cannot pull back the piston in a proximal direction to the starting position which makes reuse of the device almost impossible. The reason why reuse must be avoided is naturally due to the importance of minimizing the risk of contamination or disease transfer. Another advantage with this arrangement is that no attachment and detachment between piston and piston rod in connection with exchange of the disposable parts described. This feature is made possible partly by the fact that with the invention it is not necessary to draw or aspirate liquid into the pressure chamber by a retraction of the piston but liquid can be injected positively into the pressure chamber since de-aeration can later be done.

The storage chamber may be a single chamber where the liquid medicine is stored. It may also be a two compartment (or multi compartment) chamber provided with a by pass section (or by pass sections) in order to prepare the liquid prior injection.

Different storage chambers may be provided containing different concentrations of liquid medicine. It is advantageous to use small dose volumes in that it is less painful to inject a smaller volume than a larger volume. If smaller injection volumes are used the concentration of the active substance in the liquid medicine must be higher.

Throughout the description of the present invention the high pressure jet generated by the device is arranged to penetrate the skin of a patient. However the basic principles of the invention is equally applicable when performing needle injection of liquid medicines having high viscosity, e.g. gels. If e.g. a gel is to be injected today by a needle syringe a needle having a comparatively large inner diameter must be used which might be very painful. According to an alternative embodiment of the present invention a hypodermic needle is attached in connection with the front end opening of the injector device. The connection is performed in a robust manner in order to withstand the pressure inside the pressure chamber during injection. The needle is preferably attached to the pressure chamber during the manufacture of the chamber, e.g. during a molding process. The injection procedure is the same as when performing a needle less jet injection as described above. By using a pressure chamber provided with a needle having a similar inner diameter as the front end opening of the pressure chamber a liquid having a high viscosity can be injected using a thinner needle than before. This is very advantageous in that it is less painful for the patient. The necessary pressure needed to perform the needle injection according to the alternative embodiment is inter alia dependent of the inner diameter of the needle and the viscosity of the liquid gel.

Typical maximum pressures in the pressure chamber are in general above 25 atm (2,5 MPa), often above 50 atm (5 MPa) or above 100 atm (10 MPa). Normally the pressures are below 1000 atm (100 MPa), often below 800 atm (80 MPa) or below 500 atm (50 MPa).

Figure 5:
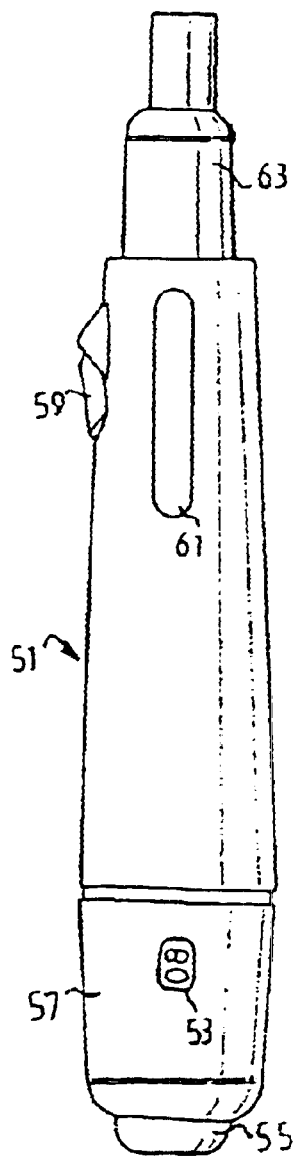
FIG. 5 illustrates the multi-dose injector device according to the invention.

FIG. 5 illustrates the multi-dose injector device according to the invention. The device comprises the housing 51 including indicator 53 indicating the size of the dose, adjustment control 55 for adjusting the dose size, a mechanism for preparing the injection 57 (controls the dosing unit and the pressurizing mechanism), a release trigger 59 that controls the pressurizing mechanism to generate the force needed for injection, an indicating window 61 and the separate unit 63.

Figure 6:
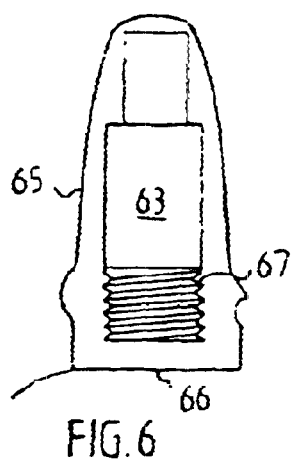
FIG. 6 shows the separate unit according to the present invention.

FIG. 6 shows the separate unit 63 in an enclosing cover 65 with a removable film 66 to maintain sterility. The separate unit 63 is adapted to be releasable attached to the housing when an injection is to be performed. Threads 67 are provided at the separate unit and corresponding threads are arranged on the inner surface of the distal end of the housing. The unit 63 is unscrewed and disposed after use.

FIGS. 7A to 7E illustrate a mechanism for dose setting, de-aeration and injection, usable with the arrangement embodiment of FIG. 3, which here corresponds to the front parts in the Figure. The device shown, generally designated 700, can be said to include a disposable part 701 and a reusable part 702 containing the mechanism and the storage chamber. With the same reference numbers as in FIG. 3 the disposable part 701 includes the pressure chamber 2 with pressure barrel 4 and piston 12 and opening 6 as well as piston rod 30 with central channel 32, rear needle 34 and support plate 36. The reusable part 702 can be said to include a housing 710 embracing a storage chamber 720 and the mechanism to be further described. The housing 710 has a front inner thread 711 for engagement with an outer thread on disposable part 701, allowing removal of a used disposable part and attachment of a fresh, during which operation the needle 34 penetrates the storage chamber membrane. The storage chamber 720, here shown with a bottleneck front, comprises a penetration membrane 722, a storage piston 724 and an open rear end 726. The mechanism can be said to include an injection unit 730, better seen in FIG. 7F, comprising a ram 731 sleeve, surrounding the storage chamber 720, having a front flange 732, arranged for push cooperation with piston rod support 36, and a rear flange 733 to be affected by a spring 736. The ram sleeve is telescopically arranged in a surrounding ram support 734, having a support flange 735 for the spring 736. The ram is axially movable with respect to the ram support and the spring is biased to propel the ram forwards, and thereby also the piston rod 30, with sufficient force to create the pressure necessary for injection. A trigger button 737 is schematically illustrated and being arranged to normally lock the ram 731 and the ram support 734 with respect to each other but when pushed allows forward movement of the ram under action of the spring. The entire injection unit 730 is arranged axially movable in the housing 710 to allow forward movement under the de-aeration step, before triggering of injection, and the housing has a slit 712 for accommodation of the externally accessible trigger 737 during such an axial movement of the injection unit 730. The mechanism can be said to further include a de-aeration unit 740, arranged to move the injection unit 730 forwards during the de-aeration step, thereby also moving the piston rod 30 forwards. The de-aeration unit 740 comprises an axially movable transition element 741, having a front end 742, for cooperation with the ram support flange 735 when pushing the injection unit forwards, and a rear push flange 743, for cooperation with a pusher to be described, and a central hole 744, allowing free axial passage around a control drum to be described. The mechanism can also be said to include a liquid transfer unit 750, arranged for displacement of storage piston 724, to affect liquid transfer from the storage chamber 720 via needle 34, central channel 32, and by-pass 38 into the pressure chamber 2, as described in relation to FIG. 3. The liquid transfer unit 750 comprises a rotationally arranged threaded plunger 751, which cooperates with a correspondingly threaded nut 752, which is axially and rotationally stationary with respect to the housing, so that a rotation of the plunger causes the plunger to move axially. The rear part of the plunger is inserted in and cooperates with the control drum, to be described, with a non-rotational connection (not shown), e.g. a non-circular connection, so that a rotation of the drum imparts a rotation on the plunger and with a one-way connection (not shown), e.g. a pawl and ratchet arrangement, so that the plunger will only rotate in the one direction causing it to move axially forwards. The mechanism can also be said to include a control unit 760, arranged to secure, in sequence, transfer of a pre-set dose volume from the storage chamber to the pressure chamber followed by de-aeration of the remaining volume in the pressure chamber. The control unit secures these actions for different set doses, i.e. a longer de-aeration stroke for small doses and a shorter de-aeration stroke for large dose volumes. The control unit can be said to include a drum 761, which is arranged axially stationary but rotational with respect to the housing. Aside from the drum features already described for cooperation with the plunger 751, the drum comprises a track 762 with a helical extension 763, a knee 764 and an axially straight extension 765. The knee 764 is axially located about where the rear push flange 743 of the transition element 741 is located before the de-aeration step. The control unit further comprises a pusher 766, arranged both axially movable and rotational with respect to the housing, having a track follower 767, arranged for cooperation with the track 762 of the drum 761, a surface 768 for cooperation with the transition element 741 and a rear thread 769 for cooperation with a correspondingly threaded part of a dose setting unit to be described as well as external helical splines (not shown) on its outer surface. When the pusher 766 is moved forwards, and when locked against rotation, from a position like that shown in FIG. 7A, the follower 767 cooperation with the helical track part 763 will first cause the drum to rotate, thereby rotating the plunger 751 to move it forwards for transfer of liquid from the storage chamber to the pressure chamber with the mechanism already described. When the follower reaches the track knee 764 no further drum rotation takes place and transfer of liquid is terminated. At the knee the follower surface 768 also engages the transition element 741 and further forward movement of the pusher will bring the transition element and the injection unit 730 forwards in the de-aeration step. The pusher is arranged to perform the same forward stroke length for every injection cycle, independent of the start position for the follower in the helical part of the track. A longer movement in the helical part of the track will give a shorter movement in the straight track part and vice versa, giving the desired relationship between dose transfer and deaeration movements. Finally the mechanism can be said to include an actuation unit 770 for dose setting and pusher movement. The actuation unit comprises a manually controlled knob 771, which can be rotated for dose setting and pushed for dose transfer and de-aeration. The knob has a screw 772 arranged for cooperation with the threaded part of pusher 766. A rotation of the knob will move the pusher to a selectable initial axial position, corresponding to the dose volume desired. Under this dose setting step the pusher 766 is allowed to rotate with the follower 767 in the helical part 763 of the track, in order to prevent that any rotation is imposed on the control drum 761. This is controlled by an inner knob sleeve 774, which is axially fixed but but rotational with respect to the knob 771, and axially movable but non-rotational with respect to the housing e.g. by use of straight splines therebetween, and has external healical splines (not shown) for cooperation with the external helical splines on the pusher surface, which helical splines have a pitch corresponding to that of helical part 763 of the track 762 and which pitches are both not self-locking whereas the pitch of the rear thread 769 is self-locking. After dose setting the pusher is axially fixed with respect to knob 771 and knob sleeve 774. A push on the knob will move the pusher 766 forwards to perform the actions described. A return spring 773 is arranged to bias the knob towards its rear position, which will bring the knob back into its rear position under reversal of the drum movement pattern, which will not move the plunger 751 backwards due to the one-way arrangement described and there is no force acting to move the piston 32 rearwards. The stroke length for the knob should correspond to the maximum stroke length for the piston 12 in the pressure barrel 4, as illustrated in FIG. 7A with arrows L. Preferably also the straight extension 765 of the track 762 should be at least of the same length, corresponding to a minimum dose and maximum de-aeration distances in the pressure chamber.

FIG. 7A shows the device before any liquid has been transferred but perhaps after a dose setting action to bring the follower 767 to an intermediate position in the helical track part 763. In FIG. 7B the knob 771 has been partially pressed to a position corresponding to full transfer of the selected dose volume. Preferably the pushing takes place by gripping the device housing and pressing it towards a support, as illustrated in the Figure, and preferably with the device in an upright position to maintain the dose transferred in the rear part of the pressure barrel 4. The illustrated height of the liquid is D, the air height is L-D as is the remaining stroke length for the knob 771. In the position shown the pusher 766 follower 767 has reached the straight part 765 of the track and has come into engagement with the transition element 741. The drum 761 has been rotated (the lower part of helical extension 763 can be seen) to bring the plunger 751 and the storage piston 724 forwards. In FIG. 7C knob 771 has been fully pressed the remaining distance L-D, corresponding to full de-aeration of the pressure chamber 4. During this movement the pusher 766 has displaced the transition element 741, the injection unit 730 with ram 731, the piston rod 30 and the piston 12 forwards a corresponding distance, to leave a remaining travelling distance of D for the piston 12 in the pressure chamber 2. Trigger 737 has moved forwards in the slit 712. During the same movement the drum 761 has been idle and non-rotating since the follower has traveled in the straight part 765 of the track 762. The needle 34 has moved away from the storage chamber as more fully described in relation to FIG. 3. In FIG. 7D the knob 771 has been released and the return spring 773 has brought it back to its extended position. This has also reversed the movements of pusher 766 and drum 761, which are now back in their initial positions but the plunger 751 and storage piston 724 are unaffected due to the one-way arrangement provided. In FIG. 7E the trigger 737 has been activated to release ram 731 from the ram support 734, allowing spring 236 to force the ram 731, the piston rod 30 and piston 12 to their final forward positions, travelling the remaining distance D. In the shown embodiment the ram support 734 and the transition element 241 are allowed to move rearwards to their initial positions under influence of the spring 236, although it is also possible to prevent such a return movement, e.g. by a latch arrangement or a one way mechanism such as a pawl and tratchet rail. The injection is now completed and the disposable part 701 can be unscrewed from the reusable part 702, the injection unit re-cocked and a new disposable part 701 attached to repeat the cycle.

The device described illustrates the preferred embodiment of arranging the deaeration mechanism in series with and behind the pressurizing mechanism so that it moves the pressure piston by moving the pressurizing mechanism forwards. Several alternatives are possible. The de-aeration mechanism can be arranged still in series but between the pressure chamber and the pressurizing mechanism and be moved forwards by elongating against the stationary pressurizing mechanism or move together with the pressurizing mechanism. The de-aeration mechanism can also be arranged in parallel with the pressurizing mechanism to act fully independent of each other in which case the pressurizing mechanism can remain stationary or be dragged forwards by the de-aeration mechanism. In all alternatives the de-aeration mechanism can move the pressure piston forwards by elongating or by moving with respect to the housing and the movements can take place by an actuation mechanism including release of stored energy or by manual influence.

Figure 8:
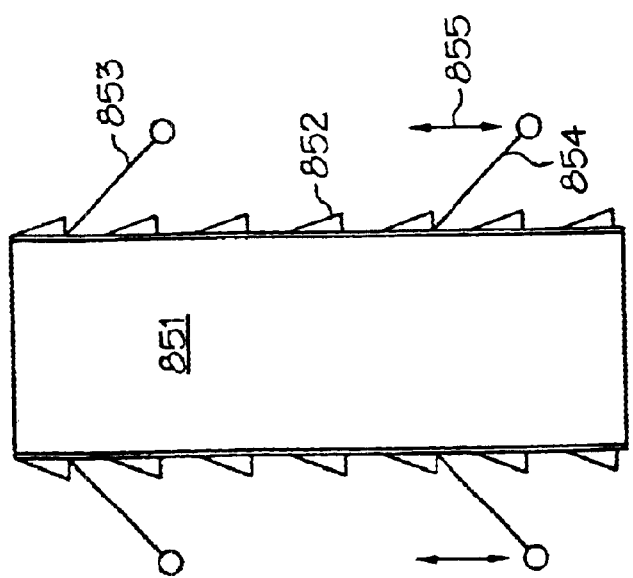
FIG. 8 illustrates schematically a prior art toothed plunger rod.

FIG. 8 illustrates schematically a prior art toothed rod and FIGS. 9A to 9D illustrates schematically a modified embodiment of that in FIG. 7, adapted for use with a toothed, rather than screw-threaded, plunger and which is compatible with both serial and parallel arrangement of pressurising mechanism and de-aeration mechanisms. As illustrated in FIG. 8 it is well known in injection or ejection devices to propel a plunger 851, having a plurality of axially spaced dents or teeth 852, by use of a system of ratchets or latches, each able to override the teeth in one direction but not in the other direction. The system shown incorporates two stationary latches 853, allowing the plunger to move forwards (upwards in the Figure) but not rearwards (downwards in the Figure), and two feeding latches 854, arranged for reciprocating movement as indicated by arrows 855, which latches brings the plunger with them during their forward movement but not during rearward movement when they instead overrides the teeth and the plunger is prevented from rearward movement by the stationary latches 853. According to a known variety, e.g. DE 19900827, the teeth and/or latches can be slightly displaced axially at different curcumferential parts of the plunger so as to allow smaller movement steps than corresponding to the distance between two teeth on one side. Any of these known constructions can be used in the embodiment to be described.

Figure 9B:
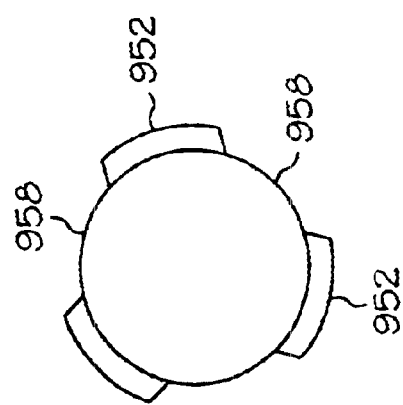
FIGS. 9A to 9D illustrates schematically a modified embodiment of that in FIG. 7, adapted for use with a toothed plunger rod.
Figure 9A:
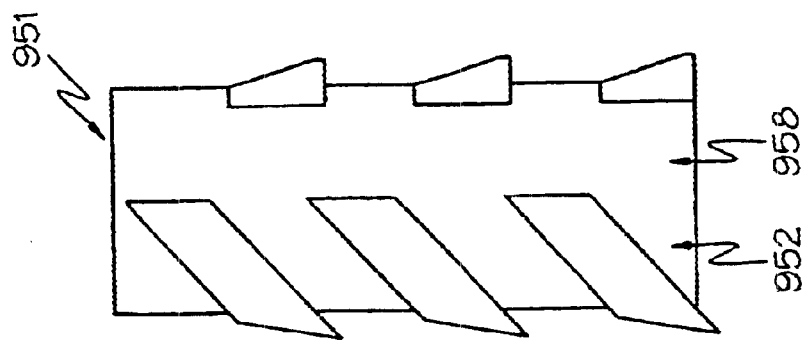

FIG. 9A shows in plain view and 9B in end view a modified plunger 951 having a generally circular cross-section and three axial sets of teeth 952 interleaved with three axial plain parts 958 distributed around the plunger periphery. Certainly any number of teeth sets and plain parts can be used, e.g. at least one and up to five. As best seen in FIG. 9A the teeth are slightly inclined with respect to the plunger axis. Such a plunger rod can be manufactured from a screw of suitable pitch with the threads removed at the plain parts. As will be further explained below the arrangement will allow latches to either engage the teeth or slide along the plain parts depending on their relative angular positions.

Figure 9D:
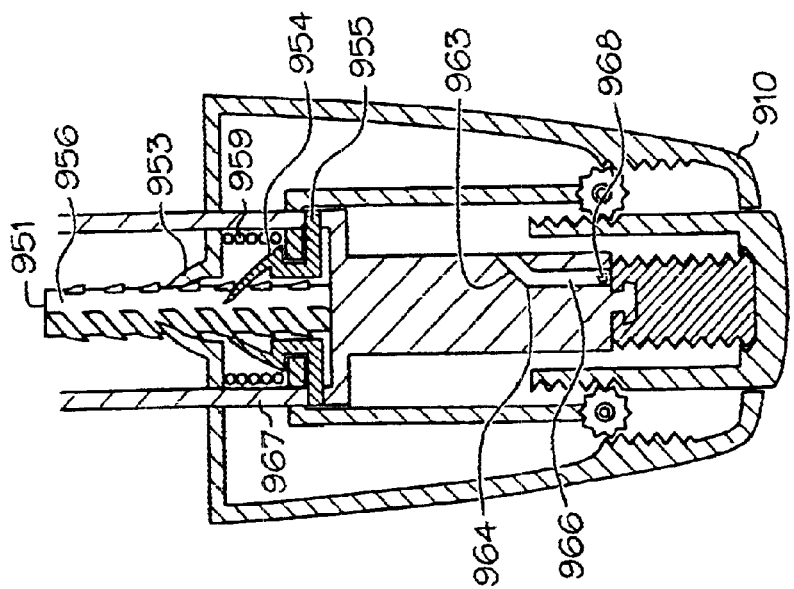
Figure 9C:
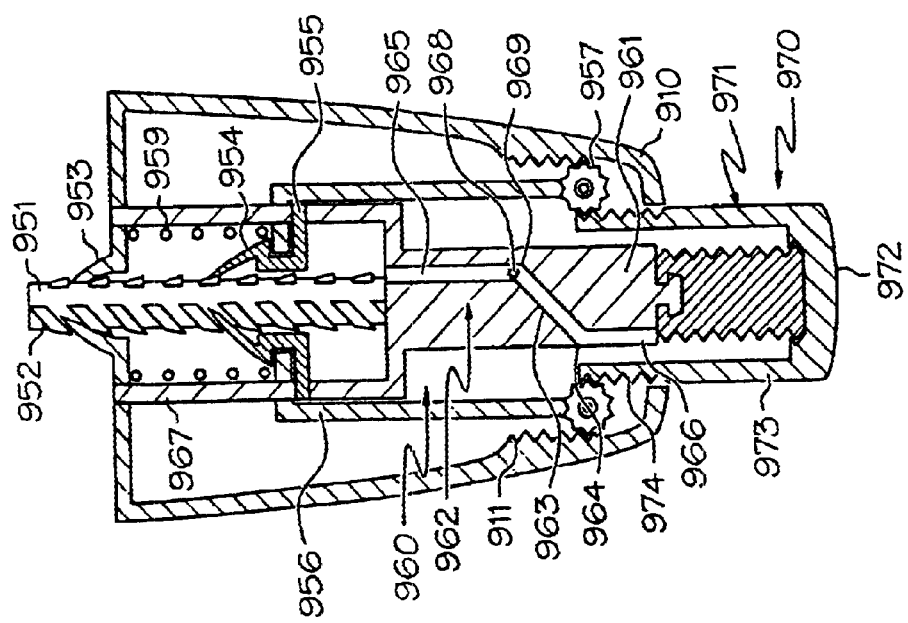

In FIGS. 9C and 9D an arrangement similar to that of FIG. 7 is shown and the following description will focus on the differences. A plunger 951, as described in relation to FIGS. 9A and 9B, is centrally arranged in the mechanism shown and has the same purpose of transferring liquid from a storage chamber to a pressure chamber as described in relation to FIG. 7. The plunger 951 is axially movable but rotationally locked in relation to the housing 910 in any manner known per se, e.g. by a part connected to the housing permanently keying in to the plain parts of the plunger. For similar purposes as explained in relation to FIG. 8, a set of three stationary latches 953 is arranged to allow forward but not rearward movement of the plunger. These latches are permanently engaged with the plunger although preferably an arrangement can be present for release in connection with plunger retraction at cartridge replacement, e.g. by allowing rotation of the plunger for release from both the stationary latches and feeding latches when the knob is in its rear position or allowing rotation of a support for the stationary latches when the knob is in its pushed, forward, position. Similarly three feeding latches 954 are arranged on a platform 955, which can both be reciprocated axially and rotated enough to either bring the feeding latches to the shown teeth engagement or to the plain parts. The platform 955 is connected to a plunger driver 956 in such a manner that it moves with the plunger driver in the axial direction but is free to rotate in relation to the plunger driver, e.g. by a bearing type attachment. To be further explained the plunger driver is driven in the axial direction by a control knob, in the shown embodiment by having a gear wheel 957 rotating between a fixed toothed housing rail 911 on the housing and a corresponding toothed knob rail on the control knob, the arrangement giving the plunger driver half the displacement of the control knob and allowing doubled pitch (axial step for one revolution) with reduced friction for the drum, to be explained. A spring 959 biases the plunger driver towards a retracted position. The platform 955 is also connected to an extension 967 of a drum 961 by which rotation can be imposed on the platform to move feeding latches 954 between the toothed parts 952 and the plain parts 958 of the plunger 951 but the extensions can move freely in the axial direction with respect to the platform. These components can be said to be part of a control unit 960 having the same purpose as in the embodiment of FIG. 7, i.e. to secure sequence of liquid transfer followed by de-aeration. In the present embodiment the drum 961 can both rotate, to engage or disengage latches 954 as described, and move axially to allow the extensions 967 to affect a de-aeration unit (not shown). The drum is preferably hollow to accommodate part of the plunger. The drum has a track 962 with a helical part 963, a knee 964, a first straight part 965 connected to the helical part at a second knee 969 and a second straight part 966. The track co-operates with a track follower 968, in this embodiment attached to the housing. When the drum is moved in the axial direction the track follower will secure a first straight movement in the track first straight part 965, with the feeding latches 954 engaged to push the plunger forwards. When the follower 968 enters into the track helical part 963 it will impose a rotation on the platform 955 to disengage the feeding latches from the plunger. Preferably the pitch of the helical part is adapted to the pitch of the inclined teeth 952 of the plunger so that disengagement can take place without axial movement of the plunger. In the present embodiment the helical part pitch is about double that of the plunger teeth pitch because of the speed and movement reduction in the gear wheel 957 system. However, it is also possible to have a slightly higher pitch on the helical part to create a liquid bleeding during disengagement, e.g. to give a fixed volume overdose independent of dose set for example to fill out dead space in the liquid transfer channel parts. Alternatively a lower pitch can be used to facilitate release of the latches. The helical part pitch should be non-locking although it is possible to fine-tune the overall friction in the system so that a locking occurs at high reaction forces, e.g. to secure that any overpressure must even out before release of the feeding latches is possible. The pitch of the plunger teeth can be non-locking but is preferably locking, to stabilise the plunger positions. When the follower reaches the knee 964 the feeding latches are disengaged and further movement in the second straight part 966 will take place without moving the plunger forwards. As in the embodiment of FIG. 7 the knee 964 is axially located where de-aeration begins, in the present embodiment where extensions 967 comes into contact with parts moving the piston in the pressure chamber. Further forward movement of the drum, with the follower in the second straight part 966 of the track, will perform de-aeration by moving the piston in the pressure chamber. Since follower movement in the helical part 963 does not, or only slightly, displace the plunger the movements in the first straight part 965 and the second straight part 966 become complementary for a given constant stroke length of the drum, such that a short movement in the first straight part (small liquid dose) corresponds to a large movement in the second straight part (long de-aeration) and vice versa. Dose setting is controlled by selection of the initial axial position for the drum. An actuation unit 970 comprises a manually controlled knob 971, which has a rotatable part 972 for dose setting, connected via co-operating threads to an axially displaceable part 973 used for dose transfer and de-aeration. Rotation of the rotateable part 972 will bring the drum 961 to a selected initial axial position with respect to the follower 968 in the first straight part 965 of the track, the position corresponding to the desired dose. The axially displaceable part 973 has external toothed knob rails 974 engaged with the gear wheel 957. Pushing the knob will rotate the gear wheel and displace the plunger driver 956 to move the plunger 951 for transfer of liquid. The displacement of plunger driver will be half of the displacement of the knob, suitable when the storage chamber has an inner cross-section area double that of the pressure chamber inner cross-section area. In operation the user first sets a dose by rotating the rotateble part 972. In FIG. 9C the position of the follower 968 in the first straight part 965 of the track corresponds to a minimum dose with the follower close to the helical part 963 of the track. The feeding latches are in engagement with the teeth 952 of the plunger 951. The knob 971 is then pushed a standardised stroke length for all doses to the position shown in FIG. 9D. During the first part of this movement the plunger is advanced, to transfer the small dose set, by co-operation of the knob rail 974, the gear wheel 957 and housing rail 911 to advance the plunger driver. When the follower passes the helical part 963 the feeding latches 954 are disengaged from the plunger teeth by rotation 60 degrees (when using three sets of teeth), as seen in FIG. 9D, and further movement of the drum, with the follower at the knee 964 and onwards in the second straight part 966 of the track, serves the de-aeration purpose. In FIG. 9D the follower 968 is in the lowermost part of the second straight part of the track, corresponding to a maximum de-aeration and maximum forward position for the extensions 967, leaving the pressure chamber ready for injection. Upon release of the knob the spring 959 will urge the knob 971, the plunger driver 956 and the drum 961 with extensions 967 back to their initial position. During this reverse motion the plunger 951 will be kept fixed by stationary latches 953 and the piston in the pressure chamber will remain in its ready position by not being attached to its driving means.

The arrangement of FIG. 9 can be used together with the remaining features of FIG. 7, not shown in FIG. 9, e.g. the same disposable pressure chamber part and replaceable storage chamber part. It can also use the same kind of injection unit 730 and de-aeration unit 740, in which case the extensions 967 of FIG. 9 will essentially act as the transition element 741 of FIG. 7, i.e. to move the entire injection unit aggregate forwards during the de-aeration step in a serial kind of arrangement. Alternatively the FIG. 9 embodiment can be combined with a parallel kind of arrangement in which the extensions 967 act independently on the piston rod support 36 during the de-aeration step and the injection unit similarly acts independently on the piston rod support during the injection step. Such an arrangement is schematically illustrated in FIG. 10.

FIG. 10 shows schematically in perspective view a modification of ram sleeve 731 of FIG. 7F, and corresponding features have been given the same reference numbers. The ram sleeve is designed to surround the storage chamber and has a front flange 732 for retention of the storage chamber and for impact on piston rod support 36 during injection. It also has a rear flange 733 to be affected by a spring (not shown), acting between the rear flange and a support (not shown), which in this embodiment can be fixed to the housing since only the ram sleeve, but not the entire injection unit shall be movable. In partial cutouts in the ram sleeve are arranged independently axially movable de-aeration rods 1001 and 1001', able to slide with respect to the ram sleeve and independently act with their front ends on the piston rod support for de-aeration purposes. The two de-aeration rods are preferably joined, as illustrated at 1002, for movement in unison. This parallel arrangement has some advantages over the serial arrangement shown in FIG. 7. During the de-aeration step the deaeration rams 1001 and 1001' will create a distance between the piston rod support 36 and flange 732 of the ram sleeve, creating an initial high penetrating liquid pressure followed by a lower sustained injection pressure. Although such a pressure profile is known as such the embodiment shows its possible implementation in the present context. A stationary support for the ram sleeve can be made simple and stable. The parallel arrangement described can be used together with the earlier described embodiments. For example, the stationary support arrangement for the ram sleeve of FIG. 10 can replace the movable support 734 of FIG. 7 and the transition element 741 can act on, be integral with or be replaced by, the de-aeration rams 1001 and 1001' or the joint 1002. Similarly the arrangement of FIG. 10 can be used with the embodiment of FIG. 9, for example if the extensions 967 are made to act on, be integral with or replaced by the de-aeration rams 1001 and 1001' or the joint 1002.

Pressure chambers for use with the invention are preferably sterilized prior to assembly and are empty or filled with air or a gas. They are preferably disposable but might also be reusable. The inner diameter of the front-end opening is 0,1–0,6 mm, preferably in the order of 0,15 mm. As said, the opening may be adapted either for needle-free jet injection, as schematically illustrated in the Figures, or needle injection, in which case the front opening may have an attachment or connector for a needle. As also known per se a short needle in the range of about 1 to 3 mm can be used to penetrate the outermost part of the skin and thereby reduce the jet speed necessary to reach target depth in the tissue.

The storage chamber is preferably separate from the pressure chamber and preferably made from different material. According to a preferred embodiment is the storage chamber made from glass, e.g. Type I glass, and the pressure chamber made from plastic, e.g. polycarbonate.

According to an alternative embodiment the storage chamber is divided, by an intermediate piston and provided with a by-pass section, into two separate compartments whereas the rear compartment comprises a liquid, e.g. water, and the front compartment comprises a solid component, e.g. a lyophilized powder. The liquid is forced into the distal compartment via the by-pass section where a liquid solves the solid component. This is a well-known procedure in the art of two compartment syringes. The thus mixed liquid located in the distal compartment is then transferred into the pressure chamber in exactly the same manner as described above.

By-pass designs, for use either in the pressure chamber or a dual compartment storage chamber, can take a variety of forms. The illustrated by-pass section roughly comprises one or many traces, by-pass channels, on the inner surface of the by-pass section of the pressure chamber. The by-pass channels can be parallel to the longitudinal direction of the delivery chamber, e.g. as described in U.S. Pat. No. 5,501,673. They could also being arranged in an angle to the longitudinal direction, e.g. as described in U.S. Pat. No. 5,716,338. The number of channels is chosen in dependence of the amount of liquid to be transferred, preferably in the order of 1–15. Many further different ways to arrange the by-pass section are known from the prior art. It is important that not too many channels are arranged due to the volume of liquid that remains in the channels when the liquid is transferred. It is also suitable to reduce the dead volume held between any circumferential ridges on the pistons by keeping the difference small between the diameter through the ridges and through the main body of the piston respectively. According to an alternative embodiment is the shape of the inner surface of the by pass section such that the piston is deformed when passing the section and thereby allows liquid to pass from the storage chamber into the pressure chamber e.g. as described in U.S. Pat. Nos. 5,472,422 and 5,817,055.

The different steps performed is basically a three step procedure comprising a transfer step where the liquid is transferred from the storage chamber into the pressure chamber, a step for removing air from the pressure chamber and an injection step. The liquid transfer and the de-aeration steps are preferably performed fairly slowly and under low pressure compared with the pressurizing step, not to induce glass breakage, plunger overshooting in the by-pass, liquid foaming or liquid spraying through the opening. Only the injection step has to be performed under high pressure.

Both during the transfer step and during the air removing step the device is preferably held in a somewhat upright position, i.e. the front end opening of the pressure chamber above horizontal, aslant or substantially facing upwards, in order to prevent the liquid to pour out.

The present invention is not limited to the above-described preferred embodiments. Various alternatives, modifications and equivalents may be used. Therefore, the above embodiments should not be taken as limiting the scope of the invention, which is defined by the appended claims.

What is claimed is:

1. An injector device for delivery of liquid from a high pressure source, the device comprising
   (a) a housing,
   (b) a pressure chamber comprising a pressure barrel for accommodation of at least one piston therein and having a front end opening for ejection of liquid, the pressure chamber being of sufficient strength to sustain the liquid pressure,
   (c) a piston inserted in the pressure barrel,
   (d) a storage chamber for liquid or liquid precursor components, the storage chamber being separate from the pressure chamber yet attached to the housing,
   (e) a conduit between the pressure chamber and the storage chamber, and
   (f) a pressurizing mechanism in the housing arranged to apply force, directly or indirectly, on the piston in the pressure barrel to create said liquid pressure, wherein
      i) the pressure chamber, the piston and at least a part of the conduit are arranged as a unit, and
      ii) the unit and the housing have corresponding fitting parts adapted for releasable attachment of the unit to the housing and the conduit to the storage chamber in a position permitting fluid connection between the storage chamber and the pressure chamber through the conduit and adapted to permit the pressurizing mechanism to act on the piston.

2. Injector device according to claim 1, wherein said piston in said pressure chamber is adapted to be moved from a medicine loading position where the liquid medicine is loaded into the pressure chamber from the storage chamber via said liquid conduit to a sealed position where the liquid conduit is closed.

3. Injector device according to claim 2, wherein air inside the pressure chamber is adapted to be expelled when the piston is in the sealed position.

4. Injector device according to claim 3, wherein said device further comprises a control arrangement wherein the volume transferred from the storage chamber to the pressure chamber is adapted to control the movement of the piston from the loading position to the sealing position so that substantially all air is expelled from the pressure chamber.

5. Injector device according to claim 1, wherein said device further comprises a dosing unit arranged to transfer an adjustable volume of liquid from the storage chamber into the pressure chamber.

6. Injector device according to claim 1, wherein the volume of liquid medicine stored in the storage chamber represents a plurality of injection doses.

7. Injector device according to claim 1, wherein the conduit comprises a by-pass section adapted to allow liquid passage around the piston.

8. Injector device according to claim 1, wherein the storage chamber is in fixed position relative the housing.

9. Injector device according to claim 1, wherein the pressurizing mechanism is adapted to act on the piston via a piston rod which can be separated from the piston to create part of the conduit and wherein the conduit comprises a needle attached to the piston rod for movement therewith.

10. Injector device according to claim 9, wherein said piston rod is provided with a central channel adapted for transfer of liquid from the storage chamber to the pressure chamber.

11. Injector device according to claim 10, wherein said piston rod is provided with a needle having a channel in connection with said central channel and adapted to penetrate a sealing membrane of said storage chamber.

12. Injector device according to claim 1, wherein the distal part of the piston rod is provided with a sealer, and wherein, in the loading position, the sealer is adapted to engage the inner surface of the pressure barrel in order to achieve a fluid tight connection for the liquid conduit.

13. Injector device according to claim 1, wherein said unit is disposable.

14. Injector unit for delivery of liquid from a high pressure, the unit comprising a pressure chamber with a pressure barrel adapted for accommodation of at least one piston therein and having a front end opening adapted for ejection of liquid, the pressure chamber being of sufficient strength to sustain liquid pressure, a piston inserted in the pressure barrel, and a conduit, wherein the unit is adapted for releasable attachment to a housing in a position permitting fluid connection between a storage chamber and the pressure chamber through the conduit and permitting a pressurizing mechanism to act on the piston, and wherein the piston or a piston rod arranged to act on the piston is adapted to allow movement between a loading position allowing open communication between the pressure chamber and the conduit and a sealed position preventing communication between the pressure chamber and the conduit.

15. Injector unit according to claim 14, wherein the pressurizing mechanism is adapted to act on the piston via a piston rod in the pressure chamber which can be separated from the piston to create part of the conduit and wherein the conduit comprises a needle attached to the piston rod for movement therewith.

16. Injector unit according to claim 15, wherein said piston rod is provided with a central channel adapted for transfer of liquid from the storage chamber to the pressure chamber.

17. Injector unit according to claim 16, wherein said piston rod is provided with a needle having a channel in connection with said central channel and adapted to penetrate a sealing membrane of said storage chamber.

18. Injector unit according to claim 17, wherein the distal part of the piston rod is provided with a sealer, wherein, in the loading position, the sealer is adapted to engage the inner surface of the pressure barrel in order to achieve a fluid tight connection for the liquid conduit.

19. Injector device according to claim 1, wherein said fitting parts comprise a corresponding screw and thread.

20. Injector device according to claim 1, wherein said fitting parts comprise a clamping connection.

21. A method for delivery of liquid from a high pressure source, the method comprising the steps of
 a) confining the liquid, or liquid precursor components, in a storage chamber,
 b) transferring the liquid from the storage chamber to a pressure chamber, initially containing gas, to only partially fill out the pressure chamber with liquid, the pressure chamber comprising a pressure barrel of substantially constant cross-section adapted for accommodation of at least one piston therein and having a front end opening for ejection of the liquid, the pressure chamber being of sufficient strength to sustain the liquid pressure, and
 c) pressurizing the pressure chamber by action on the piston in the pressure barrel to create the liquid pressure, said pressurizing step comprising
  i) moving the piston forwards with respect to the pressure chamber to substantially displace the gas therein through the front end opening, and
  ii) thereafter pressurizing the liquid in the pressure chamber for delivery of liquid through the opening.

22. Method according to claim 21, wherein before step (b), components are mixed in the storage chamber to create the liquid.

23. Method according to claim 21, wherein the force in step ii) is higher than in step i).

24. Method according to claim 21, wherein the pressure chamber is initially substantially gas filled.

25. Method according to claim 21, wherein the pressurizing step takes place while keeping the storage chamber stationary with respect to the pressure chamber.

26. Method according to claim 21, wherein the transferring step comprises the step of passing the liquid past the piston.

27. Method according to claim 26, wherein the storage chamber comprises a storage barrel of substantially constant cross-section for accommodation of at least one storage piston therein, and wherein the passing step comprises the step of moving the liquid by moving a second piston inserted in the storage barrel forwards.

28. Method according to claim 21, wherein the transferring step and the moving step are performed in sequence during a single manual movement.

29. Method according to claim 21, wherein the transferring step is preceded by a dose setting step.

30. An injector device for delivery of liquid from a high pressure source, the device comprising
 a) a housing,
 b) a pressure chamber comprising a pressure barrel for accommodation of at least one piston therein and having a front end opening for ejection of the liquid, the pressure chamber being of sufficient strength to sustain the liquid pressure,
 c) a piston inserted in the pressure barrel,
 d) a storage chamber, separate from the pressure chamber, for the liquid or liquid precursor components,
 e) a conduit between the pressure chamber and the storage chamber,
 f) a pressurizing mechanism in the housing arranged when triggered to apply force, directly or indirectly, on the piston in the pressure barrel to create said liquid pressure,
 g) a liquid transfer unit adapted to move a liquid dose from the storage chamber through the conduit to the pressure chamber, and
 h) a de-aeration mechanism adapted to move, directly or indirectly and with the pressurizing mechanism not triggered, the piston forwards a stroke distance at least corresponding to the volume not occupied by the liquid dose in the pressure chamber.

31. The device of claim 30, wherein the de-aeration mechanism is arranged in parallel with the pressurizing mechanism.

32. The device of claim 30, wherein the de-aeration mechanism is arranged in series with the pressurizing mechanism.

33. The device of claim 32, wherein the de-aeration mechanism is arranged between the piston and the pressurizing mechanism.

34. The device of claim 33, wherein the de-aeration mechanism is adapted to move the piston by elongating between the piston and the pressurizing mechanism.

35. The device of claim 31, wherein the de-aeration mechanism is arranged to the rear of the pressurizing mechanism.

36. The device of claim 35, wherein the de-aeration mechanism is adapted to move the piston by elongating between the housing and the pressurizing mechanism.

37. The device of claim 36, wherein the de-aeration mechanism is adapted to move the piston forwards by moving the pressurizing mechanism forwards.

38. The device of claim 30, wherein the de-aeration mechanism is adapted to move the piston by activation of stored energy.

39. The device of claim 30, wherein the de-aeration mechanism is adapted to move the piston by manual energy.

40. The device of claim 30, wherein the pressurizing mechanism is adapted to move the piston by activation of stored energy.

41. The device of claim 30, further comprising a control arrangement adapted to limit the piston stroke distance imposed by the de-aeration mechanism.

42. The device of claim 41, wherein the stroke distance is variable.

43. The device of claim 42, wherein the stroke distance is variable as a function of the liquid dose moved to the pressure chamber.

44. The device of claim 43, wherein the function is adapted to set the stroke distance substantially to a constant length (L) minus the axial height (D) of the liquid dose when in the pressure chamber.

45. The device of claim 43, wherein the control arrangement is adapted to be affected by the liquid dose volume for setting the variable stroke distance.

46. The device of claim 43, wherein the control arrangement is adapted to prevent activation of the de-aeration mechanism until transfer of the liquid dose has taken place.

47. The device of claim 42, wherein the stroke distance is variable by variation of a dead run for a member arranged to affect, after the dead run, directly or indirectly, the forward movement of the piston.

48. The device of claim 47, wherein the member is adapted to affect during the dead run the liquid transfer unit to transfer the dose.

49. The device of claim 48, wherein the member is adapted to perform substantially the same total movement independent of the variation of the dead run set.

50. The device of claim 30, wherein the front end opening is designed for formation of a liquid jet, with a short needle having a length of about 1 to 3 mm, or with a hypodermic needle.

51. The device of claim 30, wherein the front end opening is covered with a removable or breakable closure or sealing.

52. The device of claim 30, wherein the pressure chamber and storage chamber are made from different materials.

53. The device of claim 30, wherein said storage chamber is a dual chamber storage chamber provided with by-pass section and at least an additional piston dividing the storage chamber into two sub-chambers.

54. The device of claim 30, wherein the device is adapted for multiple doses with larger space for liquid in the storage chamber than in the pressure chamber.

55. The device of claim 30, wherein the pressure barrel has a rear liquid transfer position for the piston, in which piston position the conduit is adapted for fluid communication with the pressure barrel in front of the piston, and front sealing positions for the piston, in which piston positions the conduit is adapted for no fluid communication.

56. The device of claim 55, wherein a bypass arrangement is present in the liquid transfer position and is adapted to allow liquid to pass around the piston into the pressure chamber in front of the piston.

57. An injector device for delivery of liquid from a high pressure source, the device comprising
   (a) a housing,
   (b) a pressure chamber comprising a pressure barrel for accommodation of at least one piston therein and having a front end opening for ejection of liquid, the pressure chamber being of sufficient strength to sustain the liquid pressure,
   (c) a piston inserted in the pressure barrel,
   (d) a storage chamber, separate from the pressure chamber, for liquid or liquid precursor components,
   (e) a conduit between the pressure chamber and the storage chamber,
   (f) a pressurizing mechanism in the housing arranged to apply force, directly or indirectly, on the piston in the pressure barrel to create said liquid pressure, wherein
      i) the pressure chamber, the piston and at least a part of the conduit are arranged as a unit, and
      ii) the unit and the housing have corresponding fitting parts adapted for releasable attachment of the unit to the housing in a position permitting fluid connection between the storage chamber and the pressure chamber through the conduit and adapted to permit the pressurizing mechanism to act on the piston, and
   (g) a dosing unit adapted to transfer an adjustable volume of liquid from the storage chamber into the pressure chamber.

58. An injector device for delivery of liquid from a high pressure source, the device comprising
   (a) a housing,
   (b) a pressure chamber comprising a pressure barrel for accommodation of at least one piston therein and having a front end opening for ejection of liquid, the pressure chamber being of sufficient strength to sustain the liquid pressure,
   (c) a piston inserted in the pressure barrel,
   (d) a storage chamber, separate from the pressure chamber, for liquid or liquid precursor components,
   (e) a conduit between the pressure chamber and the storage chamber, and
   (f) a pressurizing mechanism in the housing arranged to apply force, directly or indirectly, on the piston in the pressure barrel to create said liquid pressure, wherein
      i) the pressure chamber, the piston and at least a part of the conduit are arranged as a unit,
      ii) the unit and the housing have corresponding fitting parts adapted for releasable attachment of the unit to the housing in a position permitting fluid connection between the storage chamber and the pressure chamber through the conduit and adapted to permit the pressurizing mechanism to act on the piston, and
      iii) the conduit comprises a by-pass section adapted to allow liquid passage around the piston.

59. An injector device for delivery of liquid from a high pressure source, the device comprising
   (a) a housing,
   (b) a pressure chamber comprising a pressure barrel for accommodation of at least one piston therein and having a front end opening for ejection of liquid, the pressure chamber being of sufficient strength to sustain the liquid pressure, (c) a piston inserted in the pressure barrel, (d) a storage chamber, separate from the pressure chamber, for liquid or liquid precursor components, (e) a conduit between the pressure chamber and the storage chamber, and (f) a pressurizing mechanism in the housing arranged to apply force, directly or indirectly, on the piston in the pressure barrel to create said liquid pressure, wherein
   i) the pressure chamber, the piston and at least a part of the conduit are arranged as a unit,
   ii) the unit and the housing have corresponding fitting parts adapted for releasable attachment of the unit to the housing in a position permitting fluid connection between the storage chamber and the pressure chamber through the conduit and adapted to permit the pressurizing mechanism to act on the piston, and
   iii) the pressurizing mechanism is adapted to act on the piston via a piston rod which can be separated from the piston to create part of the conduit and wherein the conduit comprises a needle attached to the piston rod for movement therewith.

60. Injector device according to claim 59, wherein said piston rod is provided with a central channel adapted for transfer of liquid from the storage chamber to the pressure chamber.

61. Injector device according to claim 60, wherein said piston rod is provided with a needle having a channel in connection with said central channel and adapted to penetrate a sealing membrane of said storage chamber.

62. Injector unit for delivery of liquid from a high pressure, the unit comprising a pressure chamber with a pressure barrel adapted for accommodation of at least one piston therein and having a front end opening adapted for ejection of liquid, the pressure chamber being of sufficient strength to sustain liquid pressure, a piston inserted in the pressure barrel, and a conduit, wherein the unit is adapted for releasable attachment to a housing in a position permitting fluid connection between a storage chamber and the pressure chamber through the conduit and permitting a pressurizing mechanism to act on the piston via a piston rod in the pressure chamber which can be separated from the piston to create part of the conduit and wherein the conduit comprises a needle attached to the piston rod for movement therewith.

63. Injector unit according to claim 62, wherein said piston rod is provided with a central channel adapted for transfer of liquid from the storage chamber to the pressure chamber.

64. Injector unit according to claim 63, wherein said piston rod is provided with a needle having a channel in connection with said central channel and adapted to penetrate a sealing membrane of said storage chamber.

65. Injector unit according to claim 64, wherein the distal part of the piston rod is provided with a sealer, wherein, in a loading position, the sealer is adapted to engage the inner surface of the pressure barrel in order to achieve a fluid tight connection for the liquid conduit.

* * * * *